US008550207B1

(12) United States Patent
Barnes

(10) Patent No.: US 8,550,207 B1
(45) Date of Patent: Oct. 8, 2013

(54) HIGH RETENTION AURAL TRANSMISSION DEVICE

(75) Inventor: Matthew Barnes, Austin, TX (US)

(73) Assignee: Hundred to One Technology, LLC, Austin, TX (US)

( * ) Notice: Subject to any disclaimer, the term of this patent is extended or adjusted under 35 U.S.C. 154(b) by 0 days.

(21) Appl. No.: 13/562,809

(22) Filed: Jul. 31, 2012

(51) Int. Cl.
*A61B 7/02* (2006.01)

(52) U.S. Cl.
USPC ............................ 181/135; 181/129; 181/130

(58) Field of Classification Search
USPC .......................................... 181/129, 130, 135
See application file for complete search history.

(56) References Cited

U.S. PATENT DOCUMENTS 1,668,890 A 5/1928 Curran et al.
3,047,089 A 7/1962 Zwislocki
4,443,668 A * 4/1984 Warren ......................... 455/351
5,298,692 A * 3/1994 Ikeda et al. ................... 181/135
6,122,388 A 9/2000 Feldman
7,068,803 B2 6/2006 Kuhlmann et al.
7,394,910 B2 7/2008 Smith et al.
D618,219 S 6/2010 Burgett et al.
8,111,863 B2 * 2/2012 Oliveira et al. ............... 381/381
2008/0152163 A1 6/2008 Mulvey
2009/0034775 A1 * 2/2009 Burton .......................... 381/380
2009/0052709 A1 2/2009 Smith
2011/0223864 A1 * 9/2011 Wai ............................. 455/41.3
2012/0087531 A1 4/2012 Hankey et al.

OTHER PUBLICATIONS

Wikipedia citation for human ear. https://en.wikipedia.org/wiki/Ear_canal.*
"Custom silicone rubbr keypads design guide" www.SiliconeDynamix.net Silicon Dynamics, Inc 61535 S. Hiughway 97 Publication date unknown.*
Burton, "AcoustiBuds" ww.burtontechusa.com/acoustibuds.html, 2 pages, copyright 2012.
Yurbuds, "Sport Earphones", http://www.yurbuds.com/, 1 page, dated Oct. 29, 2012.

* cited by examiner

*Primary Examiner* — Forrest M Phillips
(74) *Attorney, Agent, or Firm* — Craige Thompson; Thompson Patent Law Offices PC

(57) ABSTRACT

Apparatus and associated methods may relate to a unitary body having a hardness of between 20 and 35 according to the Japanese Industrial Standards (JIS) and adapted to be removably inserted into the canal 10 of an ear. In an illustrative example, the body may include a central portion between an adapter portion disposed at the proximal end of the body to couple an audio signal from an audio signal source to the central lumen. The retention portion may be disposed at a distal end of the body along a distal end axis. When inserted in the ear canal, the retention portion may be adapted to engage the canal wall between a prominence and the eardrum membrane with comfort for extended periods of time, including during physical activities, without falling out of the ear. Some embodiments by be packaged as a kit containing pairs in a range of predetermined sizes.

19 Claims, 5 Drawing Sheets

| Dimension (mm) | XS | S | M | L | XL | XXL |
|---|---|---|---|---|---|---|
| a | 7 | 7.2 | 8.6 | 9.0 | 9.0 | 9.5 |
| b | 12 | 12.3 | 12.7 | 12.7 | 13.2 | 14 |
| a' | 8.5 | 9.0 | 10.8 | 11.0 | 11.0 | 11.2 |
| b' | 5.5 | 6.5 | 7.6 | 8.3 | 9.0 | 9.6 |

FIG.6

HIGH RETENTION AURAL TRANSMISSION DEVICE

TECHNICAL FIELD

Various embodiments relate generally to aural canal inserts.

SUMMARY

Apparatus and associated methods may relate to a unitary body having a hardness of between 20 and 35 according to the Japanese Industrial Standards (JIS) and adapted to be removably inserted into the canal 10 of an ear. In an illustrative example, the body includes a central portion between an adapter portion disposed at the proximal end of the body to couple an audio signal from an audio signal source to the central lumen. The retention portion may be disposed at a distal end of the body along a distal end axis. When inserted in the ear canal, the retention portion may be adapted to engage the canal wall between a prominence and the eardrum membrane with comfort for extended periods of time, including during physical activities, without falling out of the ear. Some embodiments by be packaged as a kit containing pairs in a range of predetermined sizes.

Various embodiments may achieve one or more advantages. For example, some embodiments may provide a range of predetermined sizes to allow a user to try on various sizes to determine which ones are small enough to be comfortable, yet long enough to substantially retain the HRATD in the ear canal without falling out, e.g., during physical activity. Various embodiments may have a standard aural insert with a hardness within a range that permits extended use with substantially improved discomfort, and a shape to promote retention in the ear canal during periods of extended use. Some embodiments may provide high retention performance and substantial comfort during vigorous physical activity, such as snow boarding, for example. Some embodiments may advantageously promote high retention and significant comfort in the ear canal for a statistical majority of a human population at one of a plurality of predetermined combination of dimensioned shapes within a range of sizes. Various embodiments may provide adapters compatible for coupling to a variety of industry standard audio sources (e.g., earphone speakers). In various implementations, a user may enjoy an aural transmission device with the retention and comfort of a custom-fitted device for far less investment in time and expense than is typically required to obtain a comparable wax mold from an audiologist.

The details of various embodiments are set forth in the accompanying drawings and the description below. Other features and advantages will be apparent from the description and drawings, and from the claims.

BRIEF DESCRIPTION OF THE DRAWINGS

FIG. 6 depicts a table of exemplary dimensions for a range of sizes of the HRATD of FIGS. 3-5.

FIG. 9 depicts a cross-sectional view of an exemplary HRATD showing a central lumen there through.

Like reference symbols in the various drawings indicate like elements.

DETAILED DESCRIPTION OF ILLUSTRATIVE EMBODIMENTS

Figure 1:
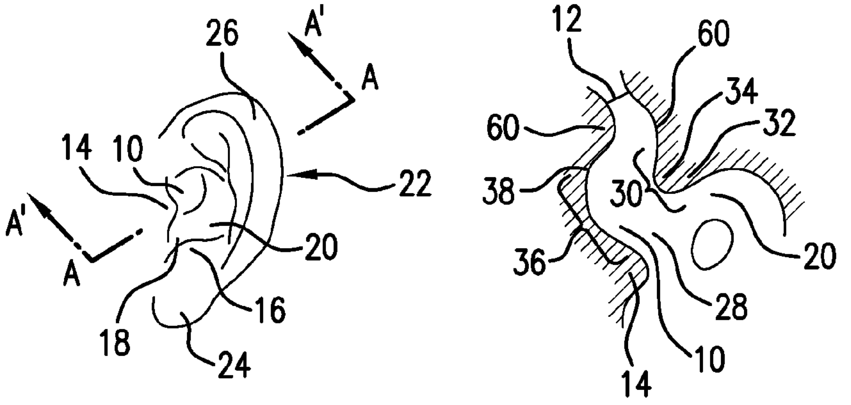
FIG. 1 depicts anatomical side and cross-sectional views of a human left ear.

FIG. 1 depicts anatomical side and cross-sectional views of an exemplary human left ear. By way of background for anatomical references made herein, FIG. 1 depicts a prior art model of a human ear canal 10 that leads to an interior eardrum membrane 12. Around the exterior of the ear canal 10, the figure depicts a tragus 14, anti-tragus 16, incisura 18, concha 20, pinna 22, and pendant lobe 24. In the interior cross-section view, taken along section line A'-A', the figure depicts an outer end 28 of the canal 10, a prominence 30, skull portion 32, a tip 34 of the prominence 30, a generally concave surface portion 36, pain sensitive cavity 38, and a region 60 between the prominence 30 and the eardrum membrane 12. Further description may be found with reference to FIGS. 1-2 of U.S. Pat. No. 5,298,692 to Ikeda, et al., the entire disclosure of which is incorporated herein by reference.

Figure 2:
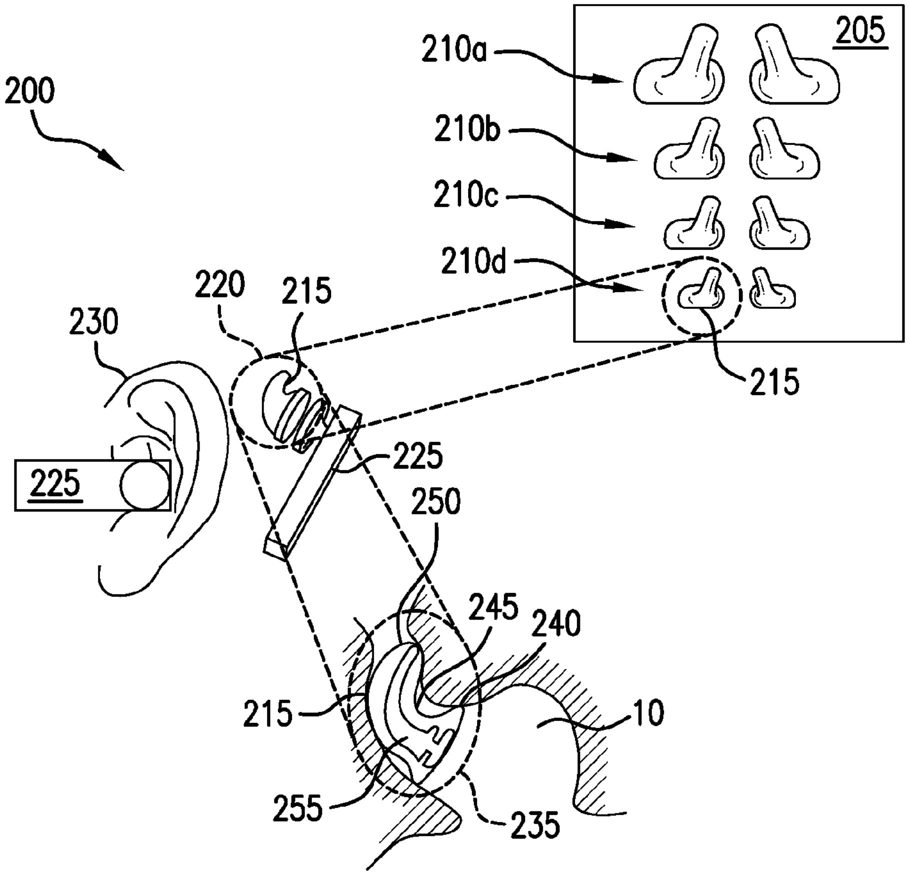
FIG. 2 depicts an exemplary kit of high retention aural transmission devices (HRATDs) of a range of sizes for comfortable fit with high retention when inserted into a human ear while coupling to an audio source.

FIG. 2 depicts an exemplary kit of high retention aural transmission devices (HRATDs) of a range of sizes for comfortable fit with high retention when inserted into a human ear while coupling to an audio source. In the depicted example, a kit 200 includes a sealable package 205 that encloses 4 pairs of HRATDs 210*a*-210*d*. Each pair of the HRATDs 210*a*-210*d* includes an exemplary HRATD adapter for insertion and retention in the left and right ears, respectively. Each of the pairs 210*a*-201*d*, respectively, is sized to be comfortably retained in a different size ear canal, such as the ear canal 10 described with reference to FIG. 1. Examples of dimensions for each size of ear are described in further detail with reference to FIGS. 3-7 and 9.

For purposes of an illustrative example, a left HRATD 215 is depicted in further detail in a detail view 220. As depicted, the HRATD 215 couples to an audio output device 225. The depicted audio output device 225 is a wireless receiver (e.g., Bluetooth), but may be wired or wirelessly connected to receive audio information from a remote signal source. The HRATD 215 mechanically couples to the audio source by receiving a male interface to a female adapter. The HRATD 215 is configured to be inserted into a right ear 230. It may be appreciated that the corresponding size right HRATD 215 in the kit 200 may be similarly coupled to an audio source and inserted into the opposing left ear.

By providing a range of sizes for the pairs 210*a*-210*d*, the kit 200 may advantageously provide a user the ability to rapidly determine a user-preferred combination of comfortable fit and adequate retention in the ear. As will be described in further detail with reference to FIGS. 3-7 and 9, for example, a user may try on various sizes to determine which ones are small enough to be comfortable, yet of adequate dimensions to substantially retain the HRATD 215 in the ear canal 10 without falling out, e.g., during physical activity.

As seen in detail view 235, the HRATD 215 is formed as a unitary body that includes an adapter portion 240, a central portion 245, and a retention portion 250. The HRATD 215 further includes a central lumen 255 extending from a proximal end of the body to a distal end of the body to provide fluid communication from a region external to the canal 10.

The HRATD 215 may be formed as a unitary body having a hardness of between 20 and 35 according to the Japanese Industrial Standards (JIS) and adapted to be removably inserted into the canal 10 of an ear. The central portion 245 is disposed along the length of the body between the adapter portion 240 and the retention portion 250. The adapter portion 240 is disposed at the proximal end of the body to couple an audio signal from an audio signal source to the central lumen. The retention portion 245 is disposed at a distal end of the body along a distal end axis. When inserted in the ear canal, the retention portion 245 may be adapted to engage the canal wall between a prominence 30 and the eardrum membrane 12.

In an illustrative example, a properly fitted distal end may extend at least 5 millimeters into the canal 10 past a tip 34 of the prominence 30. This extension past the prominence 30, in combination with a reduced hardness, may, in various examples, substantially improve retention performance without significantly sacrificing comfort.

Figure 3:
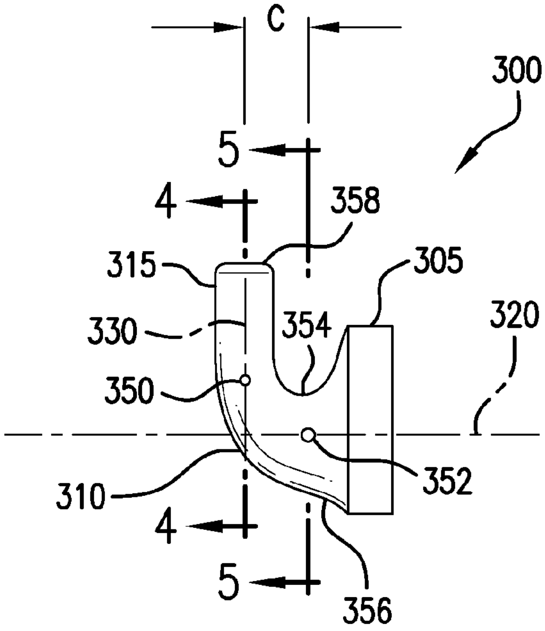
FIG. 3 depicts a side view of an exemplary HRATD.

FIG. 3 depicts a side view of an exemplary HRATD. In the depicted example, an HRATD 300 includes a unitary body having an adapter portion 305, a central portion 310, and a retention portion 315. A proximal axis 320 is centrally located within an aperture in the adapter portion 305, the aperture in the adapter portion being in fluid communication with an aperture in the retention portion 315 via a central lumen 325 that extends through the regions 305-315. A distal axis 330 is centrally located through the aperture in the retention region.

The lumen 325 in the adapter region 305 is approximately symmetrical about the proximal axis 320. The lumen 325 in the retention region 315 is approximately symmetrical about the distal axis 330. The central lumen 325 between the adapter region 305 and the retention region 315 generally follows the curvature of the central region 310.

Figure 4:
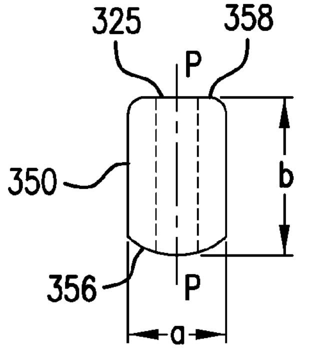
FIGS. 4-5 depict exemplary cross-sectional views of the HRATD of FIG. 3.
Figure 5:
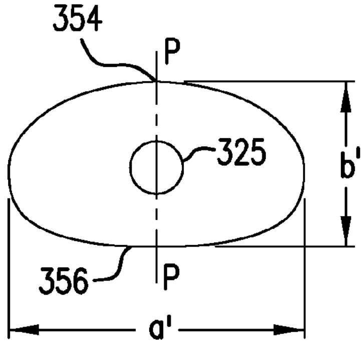

FIGS. 4 and 5 represent cross-sectional views taken through a distal axis point 350 and a proximal axis point 352, respectively.

In the side view of FIG. 3, the upper surface of the HRATD 300 is concave upward, with a valley 354 (low point). The cross-section of FIG. 5 passes through valley 354 and proximal axis point 352, and extends down to a generally upward sloping bottom surface 356 of HRATD 300.

In the side view of FIG. 3, the surface of the HRATD 300 terminates in a distal end 358. The cross-section of FIG. 4 passes through distal end 358 and distal axis point 350, and extends down to the bottom surface 356.

A dimension “c” is defined as the distance between planes of cross-section for FIGS. 4 and 5. By way of example, the dimension “c” may be from about 4 to about 6 mm.

FIGS. 4-5 depict exemplary cross-sectional views of the HRATD of FIG. 3. In FIG. 4, a dimension “b” in this example is defined as the distance between the distal end 358 and the bottom surface 356 along the distal axis 330. A dimension “a” is defined in this example as a width of the body in the retention region 315. In various examples, the “b” dimension may be at least about 10 mm.

In FIG. 5, a dimension “b'” in this example is defined as the distance between the valley 354 and the bottom surface 356 in the cross-section of FIG. 5. A dimension “a'” is defined in this example as a width of the body in the adapter region 305, as indicated in the cross-section of FIG. 5.

FIG. 6 depicts a table of exemplary dimensions for a range of sizes of the HRATD of FIGS. 3-5. As depicted, in various embodiments, the least difference in any size between b to b' is 5 mm, and the greatest insertion depth difference (b-b') is 7.4 mm. In some implementations, such as where the valley point 354 is in intimate contact with the prominence tip 34, the insertion depth difference may, for example, approximate the distance for a plane tangential to the prominence tip 34 to the distal end 358.

In various embodiments, the insertion depth difference (b-b') may preferably be about 5.0, 5.2, 5.4, 5.6, 5.8, 6.0, 6.2, 6.4, 6.6, 6.8, 7.0. 7.2, or about 7.4. In some implementations, the insertion depth difference may be between 4 mm and 10 mm, such as between about 5 and about 8 mm.

In various embodiments, the increased insertion depth achieved past the prominence tip 34 may advantageously improve retention. To improve comfort with increased insertion depth, various embodiments may further provide for a reduced hardness of less than 35, such as between about 20 up to 35, such as for example, about 25 to about 33, or preferably about 30 on the JIS (Japanese Industrial Standard). In some embodiments the hardness may be approximately 20, 21, 22, 23, 24, 25, 26, 27, 28, 29, 30, 31, 32, 33, 34, or about 35.

Figure 7:
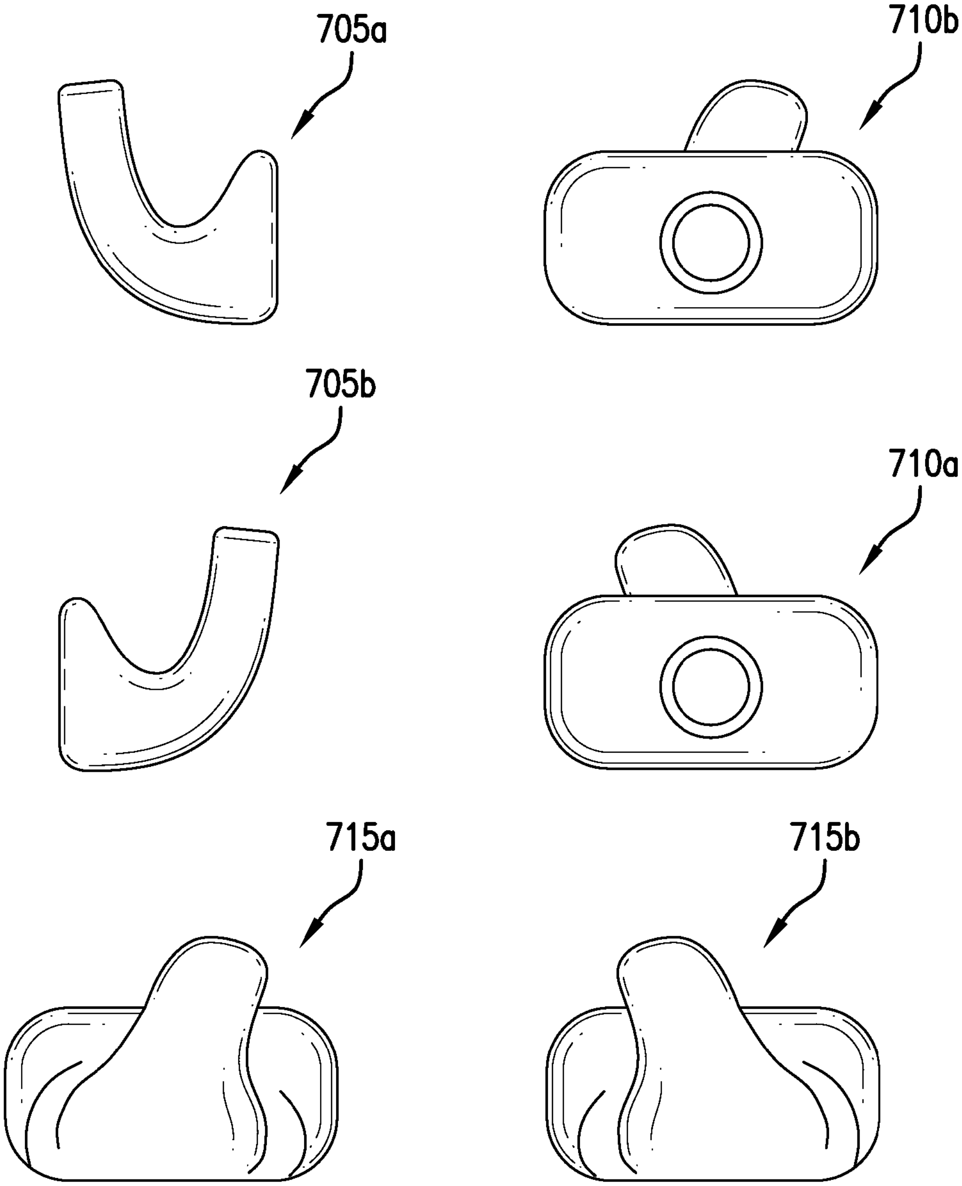
FIG. 7 depicts back, side and front views, respectively, of left and right HRATDs, according to one exemplary embodiment.

FIG. 7 depicts back, side and front views, respectively, of left and right HRATDs, according to one exemplary embodiment.

In the depicted example, a left HRATD **705*a* and a right HRATD 705*b*** are shown in side views. An overall maximum height is 15.6 mm, a maximum height of the adapter region is 9.8 mm, and height taken along the cross section through the valley point is 6 mm. A linear distance at the closest points on a flared flange of the adapter region to a distal end in the retention region is 6.5 mm. A width at the distal end is 4.8 mm, and overall width is 11.7 mm, in this example.

In the depicted example, a left HRATD **710*a* and a right HRATD 710*b*** are shown in back views. An overall maximum width of the flared flange of the adapter region is 13.4 mm, in this example.

In the depicted example, a left HRATD **715*a* and a right HRATD 715*b*** are shown in front views. The dimensions are as given above.

Figure 8:
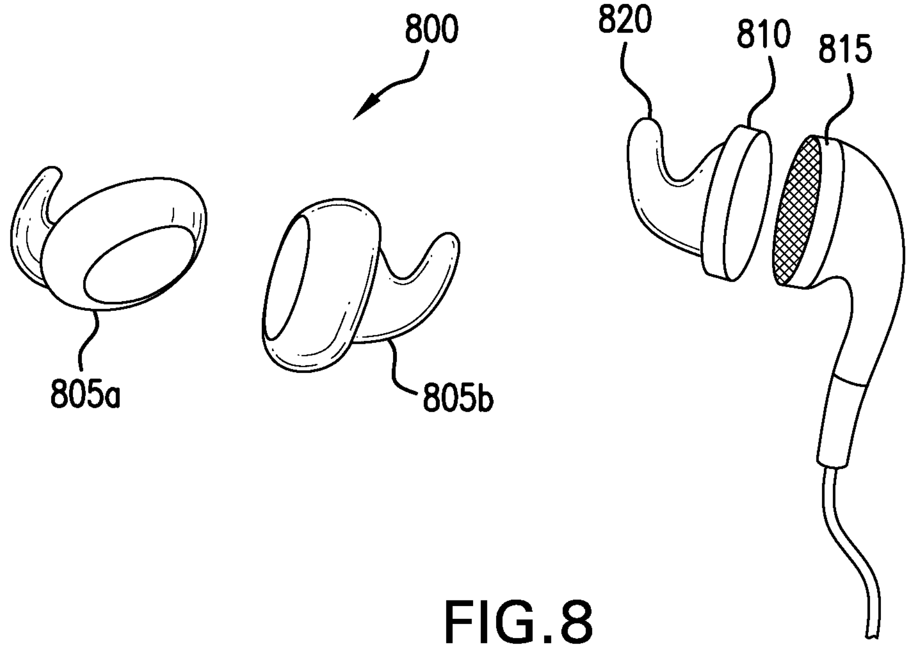
FIG. 8 depicts an exemplary left and right pair of HRATDs adapted to be releasably coupled to an audio source.

FIG. 8 depicts an exemplary left and right pair of HRATDs adapted to be releasably coupled to an audio source. In the depicted embodiment, a pair 800 of HRATDs **805*a*, 805*b*. The HRATDs include an adapter region 810 that provides a female adapter for coupling to an industry standard headphone device 815, which is commercially available, for example, from Apple, Inc. of California. The headphone device supplies audio signals that couple through the central lumen of the HRATDs 805 and are thus delivered efficiently through to a distal end 820 of the HRATD. The improved retention features of the HRATD may advantageously promote the secure coupling of the audio source, e.g., headphone device 815, in audio communication with the user’s ear canal 10**.

Figure 9:
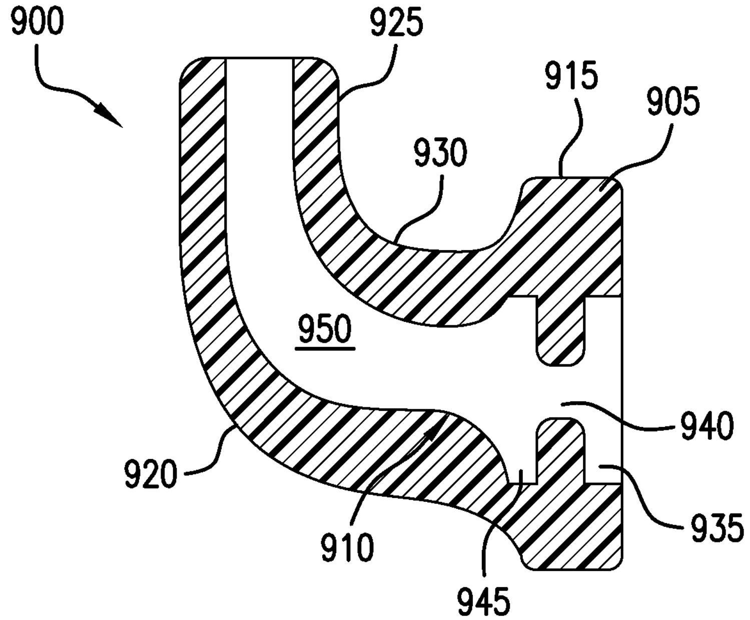

FIG. 9 depicts a cross-sectional view of an exemplary HRATD showing a central lumen there through. In this example, an HRATD 900 includes a unitary body 905 that defines a central lumen 910 through an adapter portion 915, a central portion 920, and a retention portion 925, with a substantially concave portion including a valley point 930.

In the adapter portion 915 of this example, a proximal end of the lumen 910 includes a first aperture 935 having a depth of about 1.5 mm and an inner diameter of about 5.7 mm, a duct 940 having a depth of about 1.5 mm and an inner diameter of about 2.8 mm, a second aperture 945 having a depth of about 1.5 mm and an inner diameter of about 5.7 mm, and a distal lumen portion 950 having a depth of about 1.5 mm and an inner diameter that monotonically decreases from about 5.7 mm to about 3.0 mm.

Although various embodiments have been described with reference to the Figures, other embodiments are possible. For example, aural retention devices may, in some embodiments, be adapted to be comfortably retained in the ear canal of another species, such as a dog, for example. Embodiments may be adapted for non-human ear canals, depending, in part, on the curvature and sensitivity to pain of the ear canal of some species or breeds of animals.

Some implementations may be formed without a sound transmission lumen. For example, some embodiments may serve as ear plugs to protect sensitive ear components from damage due to loud sounds. In such embodiments, the shapes described with reference to the figures may be substantially unchanged, but without the lumen. In some implementations, a sound-dampening filler may be substituted for the lumen. For example, a viscous liquid or granular filler (e.g., sand) or fiber (e.g., cotton) may be substituted in place of the lumen or other spaces or voids interior to the body of the device.

In a kit of HRATDs of various sizes, the hardness of each pair may be a function of size. For example, hardness may be the same or decrease, based upon material selection or formation, as the size increases. Accordingly, such embodiments may be substantially more compliant with increasing size within a given kit having a distribution of sizes contained therein.

Although some embodiments may be sold as kits of prefabricated sizes, some embodiments may be sold in pairs or individual left or right HRATDs, for example. In an illustrative example, a user who has already identified a desired size may directly purchase a selected size. In some embodiments, the user may select a preferred dimension of a, a', b, b', and c according to a predetermined and/or prefabricated. Some embodiments may be mass produced.

By way of example and not limitation, various embodiments may be formed, for example, materials such as silicone rubber, elastomers, polymers, medical grade silicones, or such materials in combination. Some implementations may be molded using various techniques (e.g., injection molding, vulcanization).

In various kit embodiments, the number of pairs included may include, for example, at least 3, such as 4, 5, 6, 7, 8, 9, or 10 pairs. The number of different combinations of dimensional sizes included in a kit may be, for example, at least 2, such as 3, 4, 5, 6, 7, 8, 9, or 10.

Although various embodiments have been depicted in the figures as having a substantially 90 degree bend in the central region between the adapter region and the retention region, other angles are possible. For example, some embodiments may be formed with an elbow angle of between about 70 to 130 degrees, for example, such as between about 80 and about 120 degrees, or preferably between about 85 and 115 degrees, for example.

Some embodiments may be formed to have differentiated hardnesses in different regions. For example, different hardnesses may be employed in the adapter region for coupling to a sound device than the distal end in the retention region Within a kit, the hardness characteristics of each embodiment may be substantially similar within one kit. Within a single device, the outside hardness may be between 20-35, for example. In some examples, the interior in the adapter region 915 may be of an elevated hardness. The interior surfaces may have a hardness in the range about 40-60 to retain the connection to the interior surfaces in the 935, 940, 945 to hold the device in FIG. 9. The adapter region 810 in the embodiment depicted, for example, in FIG. 8, may be formed substantially throughout from a material having a hardness of about 30, for example, such as between about 20-35.

In various embodiments, a ratio k=b/a, and k'=b'/a'. In various examples, k is at least about 1.4 or more. The ratio k may be advantageously increased to improve retention by interference in the wall past the prominence tip 34, for example. The bottom surface 356 may further, in some examples, interfere with the concave surface portion 36 and/or the valley point 354 may interfere with the prominence tip 34.

In certain embodiments, apparatus and methods may involve aural retention devices for hearing aid devices, for example.

Various examples may include a pair of left and right HRATDs that are substantially mirror image shapes of each other, whereby the left and right are not interchangeable in the opposite ear.

Various embodiments are formed in a substantially elliptical shape in at least a portion of the distal, central, and/or proximal portions. In some embodiments, an elliptical form factor may advantageously stabilize against rotation within the ear canal.

In some implementations, a proximal portion, which may include the adapter portion, may include a flared flange, which may advantageously control or limit the insertion depth of the distal end within the canal. This may advantageously prevent insertion further than intended in the ear canal.

In an exemplary embodiment, a kit, such as the kit 200 of FIG. 2 may include multiple pairs in multiple predetermined sizes selected to provide a number of insertion depth differences.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Not all drawings are necessarily to scale, and proportions may be exaggerated for illustration purposes. Accordingly, other implementations are within the scope of the following claims.

What is claimed is:

1. A high retention aural transmission device, comprising:

a unitary body having a hardness of between 20 and 35 according to the Japanese Industrial Standards (JIS) and adapted to be removably inserted into a canal of an ear, the body defining a central lumen extending from a proximal end of the body to a distal end of the body to provide fluid communication from a region external to the canal, wherein the body comprises:

(a) an adapter portion disposed at the proximal end of the body to couple an audio signal from an audio signal source to the central lumen;

(b) a retention portion disposed at a distal end of the body along a distal end axis, and when inserted in the ear canal, the retention portion is adapted to engage the canal wall between a tip of a prominence of the ear and a membrane of the eardrum; and, (c) a central portion disposed along the length of the body between the adapter portion and the retention portion and defining a valley point in a concave structure formed between the adapter portion and the retention portion, wherein the distal end extends at least 5 millimeters into the canal past the tip of the prominence, wherein the unitary body is adapted to engage the canal wall on a concave surface portion located generally opposite the prominence.

2. The device of claim 1, wherein the hardness is between about 25 and about 33.

3. The device of claim 1, wherein the hardness is about 30.

4. The device of claim 1, wherein the adapter portion further comprises a retention feature to releasably retain a mini headphone speaker.

5. The device of claim 4, wherein the adapter comprises a female adapter.

6. The device of claim 1, wherein at least a portion of the body comprises a substantially elliptical cross-section to resist rotation in the ear canal.

7. The device of claim 1, wherein a maximum dimension of the body in a plane that includes the distal axis is at least 10 mm.

8. The device of claim 1, wherein a maximum dimension of the body in a plane that includes the distal axis is at least 12 mm.

9. The device of claim 1, wherein a maximum dimension of the body in a plane that includes the distal axis is between about 12 and about 14 mm.

10. The device of claim 1, wherein the ear is a left ear of a human body.

11. The device of claim 1, wherein the ear is a right ear of a human body.

12. A kit for a high retention aural transmission device, the kit comprising:

at least 6 unitary bodies, each body having a hardness of between 20 and 35 according to the Japanese Industrial Standards (JIS) and adapted to be removably inserted into a canal of an ear, the body defining a central lumen extending from a proximal end of the body to a distal end of the body to provide fluid communication from a region external to the canal, wherein each of the at least 6 bodies comprises:

(a) an adapter portion disposed at the proximal end of the body to couple an audio signal from an audio signal source to the central lumen;

(b) a retention portion disposed at a distal end of the body along a distal end axis, and when inserted in the ear canal, the retention portion is adapted to engage the canal wall between a tip of a prominence of the ear and a membrane of the eardrum; and, (c) a central portion disposed along the length of the body between the adapter portion and the retention portion and defining a valley point in a concave structure formed between the adapter portion and the retention portion, wherein the distal end extends at least 5 millimeters into the canal past the tip of the prominence, wherein the unitary body is adapted to engage the canal wall on a concave surface portion located generally opposite the prominence.

13. The kit of claim 12, wherein the hardness is between about 25 and about 33.

14. The kit of claim 12, wherein the hardness is about 30.

15. The kit of claim 12, wherein at least a portion of the body comprises a substantially elliptical cross-section to resist rotation in the ear canal.

16. The kit of claim 12, wherein a maximum dimension of the body in a plane that includes the distal axis is at least 10 mm.

17. The kit of claim 12, wherein a maximum dimension of the body in a plane that includes the distal axis is at least 12 mm.

18. The kit of claim 12, wherein a maximum dimension of the body in a plane that includes the distal axis is between about 12 and about 14 mm.

19. The kit of claim 12, the adapter portion further comprising one or more retention features configured to retain the audio signal source.

* * * * *